US009633172B2

(12) United States Patent
Overfield et al.

(10) Patent No.: US 9,633,172 B2
(45) Date of Patent: Apr. 25, 2017

(54) PHARMACY AUTOMATION OPTIMIZATION SYSTEM AND METHOD

(71) Applicant: Parata Systems, LLC, Durham, NC (US)

(72) Inventors: Keith E. Overfield, Raleigh, NC (US); Brian Cristobal, Raleigh, NC (US); Donald Blandford, Jr., Raleigh, NC (US)

(73) Assignee: Parata Systems, LLC, Durham, NC (US)

( * ) Notice: Subject to any disclaimer, the term of this patent is extended or adjusted under 35 U.S.C. 154(b) by 1007 days.

(21) Appl. No.: 13/682,949

(22) Filed: Nov. 21, 2012

(65) Prior Publication Data

US 2013/0325170 A1  Dec. 5, 2013

Related U.S. Application Data

(60) Provisional application No. 61/655,673, filed on Jun. 5, 2012.

(51) Int. Cl.
*G06F 19/00* (2011.01)
*G06Q 10/08* (2012.01)
(Continued)

(52) U.S. Cl.
CPC ...... *G06F 19/3456* (2013.01); *G06F 19/3462* (2013.01); *G06Q 10/087* (2013.01);
(Continued)

(58) Field of Classification Search
None
See application file for complete search history.

(56) References Cited

U.S. PATENT DOCUMENTS 5,337,919 A  8/1994 Spaulding et al.
5,907,493 A *  5/1999 Boyer et al. .................. 700/231
(Continued)

FOREIGN PATENT DOCUMENTS

WO  WO 2004/015505 A2  2/2004

OTHER PUBLICATIONS

Notification of Transmittal of the International Search Report and the Written Opinion of the International Searching Authority, or the Declaration, PCT/US2013/042189, Date of Mailing: Aug. 19, 2013, 8 pages.

*Primary Examiner* — Patrick Cicchino
(74) *Attorney, Agent, or Firm* — Myers Bigel, P.A.

(57) ABSTRACT

A method of assessing the productivity of a pharmacy includes: (a) recording information regarding the identity and quantity of each pharmaceutical being automatically dispensed with an automated prescription monitoring unit; (b) with an overall pharmacy prescription monitoring unit, recording information regarding (i) dispensing of pharmaceuticals dispensed from the automated pharmacy machine and (ii) manual dispensing of pharmaceuticals; (c) identifying in step (a) low performing pharmaceuticals; (d) identifying in step (b) high performing pharmaceuticals dispensed manually as candidates for automated dispensing; (e) comparing low performing pharmaceuticals of step (c) with high performing pharmaceuticals of step (d) to determine whether replacement is recommended; (f) confirming whether high performing pharmaceuticals identified in step (d) are capable of automated dispensing; and (g) replacing in the automated pharmacy machine a low performing pharmaceutical identified in step (c) with a high performing pharmaceutical identified in step (d).

17 Claims, 2 Drawing Sheets

(51) Int. Cl.
    *G07F 7/00*           (2006.01)
    *G07F 11/00*         (2006.01)
    *G07F 9/02*           (2006.01)
    *G07F 17/00*         (2006.01)

(52) U.S. Cl.
    CPC ............ *G07F 9/026* (2013.01); *G07F 11/002* (2013.01); *G07F 17/0092* (2013.01)

(56) References Cited

U.S. PATENT DOCUMENTS

| | | |
|---|---|---|
| 6,006,946 A | 12/1999 | Williams et al. |
| 6,176,392 B1 | 1/2001 | Williams et al. |
| 6,306,812 B1 | 10/2001 | Williams et al. |
| 6,330,491 B1 * | 12/2001 | Lion ............................. 700/237 |
| 6,971,541 B2 | 12/2005 | Williams et al. |
| 7,596,932 B2 | 10/2009 | Sink |
| 7,689,317 B2 * | 3/2010 | McGrady et al. ............ 700/236 |
| 7,827,041 B2 * | 11/2010 | Roberts et al. ................... 705/2 |
| 7,860,724 B2 * | 12/2010 | Chudy et al. ..................... 705/2 |
| 8,016,095 B2 | 9/2011 | Daniels |
| 8,165,929 B2 * | 4/2012 | Chudy et al. ................... 705/28 |
| 8,744,618 B2 * | 6/2014 | Peters et al. .................. 700/236 |
| 8,954,190 B2 * | 2/2015 | Braunstein .................... 700/242 |
| 8,989,896 B2 * | 3/2015 | Brown ........................... 700/242 |
| 2004/0088187 A1 * | 5/2004 | Chudy et al. ..................... 705/2 |
| 2004/0133705 A1 * | 7/2004 | Broussard et al. ............... 710/1 |
| 2006/0293784 A1 * | 12/2006 | Braunstein .................... 700/231 |
| 2008/0110555 A1 | 5/2008 | Bouchelle et al. |
| 2008/0110921 A1 | 5/2008 | DuMond et al. |
| 2008/0283179 A1 | 11/2008 | Sink |
| 2015/0005935 A1 * | 1/2015 | Bae et al. ..................... 700/241 |

* cited by examiner

PHARMACY AUTOMATION OPTIMIZATION SYSTEM AND METHOD

RELATED APPLICATION

The present application claims the benefit of and priority from U.S. Provisional Patent Application No. 61/655,673, filed Jun. 5, 2012, the disclosure of which is hereby incorporated herein in its entirety.

FIELD OF THE INVENTION

The present invention relates generally to the dispensing of pharmaceutical prescriptions, and more particularly to the automated dispensing of pharmaceutical prescriptions.

BACKGROUND OF THE INVENTION

Automation is used in pharmacies to generate operational efficiency for the process of filling prescriptions. Exemplary automated pharmacy machines are described and illustrated in U.S. Pat. No. 5,337,919 to Spaulding et al., U.S. Pat. Nos. 6,006,946; 6,036,812; 6,176,392 and 6,971,541 to Williams et al., U.S. Pat. No. 8,016,095 to Daniels, U.S. Pat. No. 7,596,932 to Sink, and U.S. Patent Publication Nos. 2008/0110921; 2008/0110555; and 2008/0283179, the disclosure of each of which is hereby incorporated herein in its entirety.

To make a pharmacy as efficient as possible, an automation system must incorporate the appropriate mix of drugs that generate the greatest amount of prescriptions processed through the automation with limited "touch time." Often, at installation of automated equipment, the correct mix of NDCs within the automated machine is determined by a snapshot of the pharmacy's recent prescription drug dispensing history. With some equipment, although individual drug dispensing cells (or bins) are configurable onsite, pre-calibration of the dispensing cells occurs prior to installation based on the information supplied in the snapshot discussed above.

As time goes on, it is common in the pharmacy business to see frequent changes to a pharmacy's NDC mix. This is the result of, inter alia, new drugs released to market, new generic releases, and alternate manufacturers of existing drugs (for example, in 2011 there were 800 new unique drug products released (identified by National Drug Code (NDC) in the US or Drug Identification Number (DIN) in Canada), including brand to generic and entirely new generic drugs). Seasonal changes may also result in changes to the particular drugs most frequently dispensed by the pharmacy (e.g., allergy medications in the spring and summer months versus cold and flu medications, as well as antibiotics, during the fall and winter months). Due to the frequency of changes in NDCs, the efficiency resulting from the specific mix of NDCs originally established in the automation may deteriorate over time. For example, 50% automation throughput (as a percentage of total pharmacy volume) can drop to 30% or less over time if the NDC mix housed in the automation system never changes.

A pharmacy's ability to maintain automation optimization is difficult in the current environment. It ordinarily requires querying of the pharmacy's pharmacy management system of all prescriptions filled over a given duration (typically 90 days). The pharmacy also typically must run a report from the automation to provide a dispensing history that is specific to automated processing. The staff must then manually study the results to look for slow moving NDCs in automation and replace them with fast moving NDCs that are able to be filled through automation. Additionally, without even more complex calculations, the pharmacy will not know its current run rate (% of scripts through automation) vs. future run rate (% scripts through automation after changes) to know if the updates will have a significant or nominal impact on performance. Due to the complexity of this process of optimizing automation, most pharmacies will only perform these tasks 1-2 times per year at best, so its efficiency gains are not being maximized. It may be desirable to provide methods and systems that assist pharmacies in improving the efficiency level of their automation.

SUMMARY OF THE INVENTION

As a first aspect, embodiments of the present invention are directed to a method of assessing the productivity of a pharmacy. The method comprises the steps of: (a) during dispensing of pharmaceuticals from an automated pharmacy machine, recording information regarding the identity and quantity of each pharmaceutical being automatically dispensed with an automated prescription monitoring unit; (b) recording information regarding the identity and quantity of each pharmaceutical being manually dispensed by the pharmacy, wherein the recording is performed with a prescription monitoring unit; (c) identifying from the information recorded in step (a) low performing pharmaceuticals; (d) identifying from the information recorded in step (b) high performing pharmaceuticals dispensed manually that are candidates for automated dispensing; (e) comparing low performing pharmaceuticals of step (c) with high performing pharmaceuticals of step (d) to determine whether replacement of the low performing pharmaceutical with the high performing pharmaceutical in the automated pharmacy machine is recommended; (f) confirming whether high performing pharmaceuticals identified in step (d) are capable of automated dispensing; and (g) replacing in the automated pharmacy machine a low performing pharmaceutical identified in step (c) with a high performing pharmaceutical identified in step (d).

As a second aspect, embodiments of the present invention are directed to a system for assessing the productivity of a pharmacy, comprising: an automated pharmacy machine; an automated prescription monitoring unit associated with the automated pharmacy machine and configured to record information regarding pharmaceutical prescriptions dispensed by the automated pharmacy machine; a prescription monitoring unit configured to record information regarding manual dispensing of pharmaceuticals; and a controller associated with the automated prescription monitoring unit and the prescription monitoring unit, the controller configured to receive and compare the information recorded by the automated prescription monitoring unit and the prescription monitoring unit.

DETAILED DESCRIPTION OF EMBODIMENTS OF THE INVENTION

Figure 1:
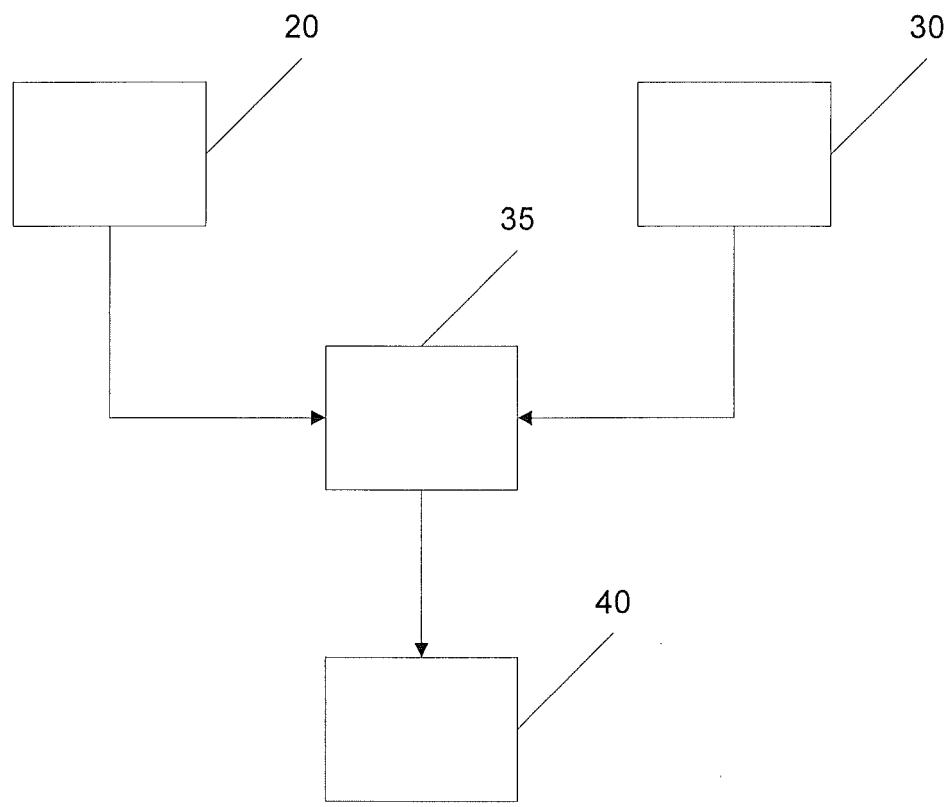
FIG. 1 is a schematic diagram of a system for monitoring pharmacy prescription frequency for automated and manually filled prescriptions according to embodiments of the present invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

As used herein, the term "forward" and derivatives thereof refer to the general direction vial carriers and vials travel as they move from station to station; this term is intended to be synonymous with the term "downstream", which is often used in manufacturing environments to indicate that certain material being acted upon is farther along in the manufacturing process than other material. Conversely, the terms "rearward" and "upstream" and derivatives thereof refer to the directions opposite, respectively, the forward and downstream directions.

Well-known functions or constructions may not be described in detail for brevity and/or clarity.

Embodiments of the present invention are directed to systems and methods for providing a pharmacy with regular (e.g., daily) feedback on automation performance and monitoring opportunities for improving pharmacy efficiency based on monitoring, in real time, NDCs able to be added into automation that are currently outside the equipment (e.g., used to manually fill prescriptions).

Referring first to FIG. 1, a system 10 according to embodiments of the invention may include four components: an overall pharmacy prescription monitoring unit 20; an automated prescription monitoring unit 30; a controller 35; and an access device 40 for retrieving data. These components are discussed in more detail below.

The overall pharmacy prescription monitoring unit 20 can be any device, such as a bar code scanner or the like, that can record the processing of all prescriptions processed by the pharmacy, whether the prescription is filled manually or via automation. As an example, a bar code scanner may be located near a cash register of a pharmacy, such that all prescriptions are scanned as the customer/patient pays for the prescription. As another alternative, a bar code scanner may be located near a prescription filling station or near a pharmaceutical verification station, as all prescriptions may require verification after filling. In other embodiments, the overall pharmacy prescription monitoring unit 20 may be associated with the pharmacy information system (PIS) of the pharmacy, and therefore may be in the form of software. Other devices and locations may also be employed.

The overall prescription monitoring unit 20 may collect information that includes the prescription's NDC# or DIN#, prescriptions filled and pills counted in a particular duration (e.g., a rolling 24 hour period).

The automated prescription monitoring unit 30 can be any device that is capable of tracking prescriptions filled via automation. The automated prescription monitoring unit is typically associated with an automated pharmacy dispensing machine, such as one of those described above. In some embodiments, the unit 30 may be a bar code scanner located within the automated pharmacy dispensing machine; as one example, the bar code scanner may be positioned at or adjacent to a location where filled prescriptions are offloaded or dropped off. In other embodiments, the automated prescription monitoring unit 30 may be associated with the PIS of the pharmacy, tracking those prescriptions sent to the automated dispensing machine for fulfillment. Other devices and locations may also be employed.

The information collected by the automated pharmacy monitoring unit 30 may include NDC# or DIN#, prescriptions filled and pills counted in the automated pharmacy dispensing machine in a particular duration (e.g., a rolling 24 hour period).

The controller 35 is configured to receive information from the overall pharmacy prescription monitoring unit 20 and the automated pharmacy prescription unit 30 and to process this information. In particular, the controller 35 may identify "low performing" pharmaceuticals dispensed via automation (i.e., via the automated pharmacy machine) and "high performing" pharmaceuticals that are dispensed manually. The controller 35 may also be configured to determine whether high performing manually dispensed pharmaceuticals can be dispensed with the automated pharmacy machine. The controller 35 may further be configured to recommend the replacement of a low performing pharmaceutical with a high performing pharmaceutical in the automated pharmacy machine.

The controller 35 may be any device that is capable of receiving data from the units 20, 30 and processing the data to produce the information discussed above. As such, the controller 35 may be a personal computer, network computer, microprocessor, or other data processing device. The controller 35 is operatively connected (e.g., hard-wired or wirelessly) to the overall pharmacy prescription monitoring unit 20 and the automated prescription monitoring unit 30 to enable the controller to receive data/information therefrom. The controller 35 may be on-site or may be located remotely from the units 20, 30.

The access device 40 (which may be optional in some embodiments) is a device or portal that enables a pharmacy to have immediate and real time access to data and results gathered from the units 20 and 30 at the controller 35. Access may be either on-site or remote as desired. Exemplary access devices include web-based dashboards, displays attached to or associated with the automated pharmacy machine and/or the PIS, or the like.

Figure 2:
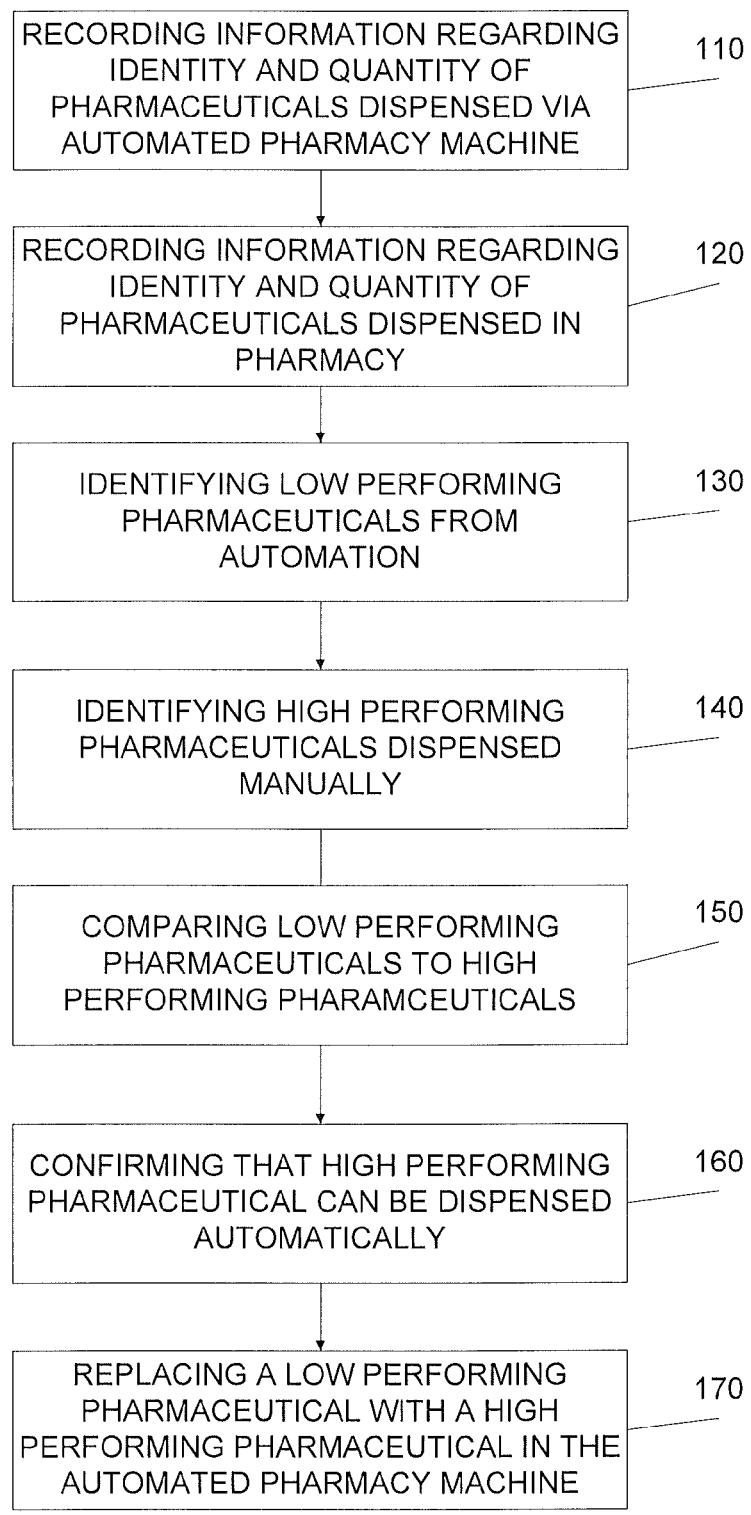
FIG. 2 is a flow chart illustrating methods of improving pharmacy dispensing frequency according to embodiments of the invention.

Referring now to FIG. 2, in operation, periodically (for example, each day at a selected time) data sets recorded from the overall prescription monitoring unit 20 and the automated prescription monitoring unit 30 representative of all of the prescriptions dispensed during the period are compiled (blocks 110 and 120). This information can be uploaded to the controller 35 (on-site or remote) where the information is logged and used to generate performance data. For example, that period's automated throughput can be calculated by comparing automated prescriptions filled to total pharmacy prescriptions filled. This percentage may be logged regularly (e.g., daily) and average percentages may be calculated on a rolling period (e.g., 90 days). "Low performing" NDCs filled with the automated pharmacy machine can be identified (block 130). "Low performing" NDCs can be identified by a performance calculation that weighs known performance attributes of automation of that NDC; performance attributes can include prescription volume, pill count, count accuracy, unit cost, replenishment frequency and cleaning code. For all prescriptions that could have been filled through automation (i.e., via the automated pharmacy machine) but were not, the frequency of dispensing each day can be logged. This can assist in identifying "high performing" NDCs that are dispensed manually (i.e., outside of automation) (block 140).

As time passes, this pharmacy data is collected and processed. Information that the pharmacy may benefit from includes: (a) current unit performance as a percentage of total scripts filled; and (b) based on the rolling period, potential performance (percentage of total scripts) if specific top moving NDCs not in automation were added to automation. The "high performing" NDCs dispensed manually are compared to "low performing" drugs currently dispensed via automation (block 150). As an example, the high performing NDC may be required to have a higher throughput than the lower performing NDC of a predetermined percentage, such as 0.5 percent, 1.0 percent, 2.0 percent, 5.0 percent, or the like. Criteria for comparing NDCs can include: quantity of prescriptions; quantity of pills dispensed; stock bottle size; replenishment frequency; cost of replacing one NDC with another; and cost of the drug itself. Also, the controller 35 can confirm that the high performing drugs are suitable for dispensing via automation (i.e., the tablets are of a shape/size/composition suitable for automated dispensing) (block 160).

Based on this data, a pharmacy can produce a report showing which low performing NDCs should be removed from automation and which high performing NDCs should be added to automation, at which point replacement can be performed (block 170). The report may also include information on the percent throughput for each of the NDCs being switched into and out of automation, as well as overall throughput improvement, to provide clarity on the quantitative change that may be realized by the switch.

For those NDCs suggested to be added to automation, recommendations also can be made as to the settings of the dispenser in the automated pharmacy dispensing machine for optimal dispensing of that NDC. For example, for an automated pharmacy machine such as that disclosed in U.S. Pat. No. 6,971,541 to Williams et al. and U.S. Pat. No. 8,016,095 to Daniels, supra, which uses individual bins or "cells" that rely on agitated air for counting and dispensing, specific settings for the outlet of the cell may be recommended to facilitate the change-over from the low performing NDC to the high performing NDC. In addition, information from the database (size of the drug) combined with information about the number of pills dispensed per prescription and frequency of dispensing can be used to determine the size of the overall bin or cell to use for dispensing the drug in automation. These recommendations can optimize performance of the system and reduce "touch time" needed for refilling of the drug cell during a given period of time.

In some embodiments, daily and historical performance may be readily available and throughput performance may be reported and/or visualized in a variety of ways. The performance can be presented, for example, for a particular time period (i.e., one day, one week, one month) as chosen by the pharmacy and the percentage of throughput for the time period can be compared to the goal for the pharmacy, thus allowing insight into whether improvement is necessary to meet set goals and the extent of such improvement. Statistics for the given time period also, for example, may be viewed against the best and worst historical performance for that length of time. Although reports may be viewed on any time scale chosen by the pharmacy, the optimized impact may be limited to monthly to reduce interaction time.

In some embodiments, in addition to single-location views, pharmacies that have multiple sites may be able to view information about any or all of their sites. For example, a large pharmacy chain may view a summary of the captured metrics across all units in its fleet and compare performance of all stores. Some examples of ways this information might be reported is to view throughput from all stores for a specific time period, as well as the goal differential for each store. The report may also include the rank of each store based on the throughput determination, goal differential, or some other criteria based on the collected data. This would provide the chain with the data it can work with to request corrective action from underperforming sites.

Based on predicted performance and success criteria, key metrics (automation optimization, replenishment interaction, etc.) may be exported to a summary report so pharmacies can independently and more readily manage their automation.

In some embodiments, key unit and/or fleet performance metrics (service-related, unit health, etc.) may be tracked, with these data available at the same portal or in the same report as optimization metrics. The relationship of service data to throughput performance can provide greater insight into why a site may be underperforming (i.e., a unit was offline for two days for upgrades or repairs causing the site to revert to manual processing.)

In some systems, additional data may be collected. For example, by collecting information regarding the number of prescriptions filled and their associated date/time stamps, hourly/daily/weekly loads can be tracked to assist with staffing. Data may also be used to assist in inventory management and/or stock bottle ordering based on average prescription usage (i.e., it may be more economical or efficient for a pharmacy to order a smaller or larger stock bottle size for a particular drug based on the frequency of usage of that pharmaceutical). Other data may also be collected and/or processed in some embodiments.

The present invention has been described herein with reference to flowchart and/or block diagram illustrations of methods, systems, and devices in accordance with exemplary embodiments of the invention. It will be understood that each block of the flowchart and/or block diagram illustrations, and combinations of blocks in the flowchart and/or block diagram illustrations, may be implemented by computer program instructions and/or hardware operations. These computer program instructions may be provided to a processor of a general purpose computer, a special purpose computer, or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer usable or computer-readable memory that may direct a computer or other programmable data processing apparatus to function in a particular manner, such that the instructions stored in the computer usable or computer-readable memory produce an article of manufacture including instructions that implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart and/or block diagram block or blocks.

It will be further appreciated that the functionality of any or all of the program modules may also be implemented using discrete hardware components, one or more application specific integrated circuits (ASICs), or a programmed digital signal processor or microcontroller. The program code may execute entirely on a single processor and/or across multiple processors, as a stand-alone software package or as part of another software package. The program code may execute entirely on an electronic device or only partly on the electronic device and partly on another device. In the latter scenario, the other device may be connected to the electronic device through a wired and/or wireless local area network (LAN) and/or wide area network (WAN), or the connection may be made to an external computer (for example, through the Internet using an Internet Service Provider).

The invention has been described with respect to a retail pharmacy location but may apply to any other type of pharmacy or setting where automated pharmacy machines may be used such as a hospital, central fill facility, mail order facility, etc.

The foregoing embodiments are illustrative of the present invention, and are not to be construed as limiting thereof. Although exemplary embodiments of this invention have been described, those skilled in the art will readily appreciate that many modifications are possible in the exemplary embodiments without materially departing from the novel teachings and advantages of this invention. For example, a variety of report formats may be implemented to convey the information provided by the system. Such formats might include, inter alia, dashboards comprised of various chart and/or table formats, gauges, etc., or chart or table style reports. Accordingly, all such modifications are intended to be included within the scope of this invention.

That which is claimed is:

1. A method of improving productivity of pharmacy, comprising the steps of:
   (a) during dispensing of pharmaceuticals from an automated pharmacy machine, recording, by at least one processor of an automated prescription monitoring unit, information regarding an identity and quantity of each pharmaceutical being automatically dispensed;
   (b) recording, by at least one processor of a prescription monitoring unit, information regarding an identity and quantity of each pharmaceutical being manually dispensed by the pharmacy;
   (c) identifying, by at least one processor of a controller operatively associated with the automated prescription monitoring unit and the prescription monitoring unit, from the information recorded in step (a), low performing pharmaceuticals;
   (d) identifying, by the processor of the controller, from the information recorded in step (b) high performing pharmaceuticals dispensed manually that are candidates for automated dispensing;
   (e) comparing, by the processor of the controller, low performing pharmaceuticals of step (c) with high performing pharmaceuticals of step (d) to determine whether replacement of a low performing pharmaceutical with a high performing pharmaceutical in the automated pharmacy machine is recommended;
   (f) confirming, by the processor of the controller, whether high performing pharmaceuticals identified in step (d) are capable of automated dispensing; and
   (g) modifying the automated pharmacy machine to replace a low performing pharmaceutical identified in step (c) with a high performing pharmaceutical identified in step (d); wherein the modifying comprises, based on a recommended modification provided by the processor of the controller, adjusting a bin of the automated pharmacy machine from which the high performing pharmaceutical is to be dispensed or replacing the bin of the automated pharmacy machine from which the low performing pharmaceutical is dispensed, further comprising the step of producing a report with information generated in steps (c)-(e).

2. The method defined in claim 1, wherein step (b) further comprises recording the identity and quantity of each pharmaceutical being automatically dispensed with the prescription monitoring unit, wherein the prescription monitoring unit is an overall pharmacy prescription monitoring unit.

3. The method defined in claim 1, wherein the information regarding the identity and quantity of each pharmaceutical being automatically dispensed in step (a) is collected by a detector located within the automated pharmacy machine.

4. The method defined in claim 1, wherein the information recorded in step (a) is at least one of: NDC number; DIN number; number of prescriptions filled; and number of tablets dispensed.

5. The method defined in claim 1, further comprising an access device operatively connected with the automated prescription monitoring unit and with the prescription monitoring unit.

6. The method defined in claim 1, wherein steps (a) and (b) are performed on a substantially regular schedule.

7. The method defined in claim 1, wherein at least one of the automated prescription monitoring unit and the prescription monitoring unit is integrated with a pharmacy information system.

8. A system for improving productivity of a pharmacy, comprising:
   an automated pharmacy machine;
   an automated prescription monitoring unit associated with the automated pharmacy machine and configured to record information regarding pharmaceutical prescriptions dispensed by the automated pharmacy machine;
   a prescription monitoring unit configured to record information regarding manual dispensing of pharmaceuticals; and
   a controller associated with the automated prescription monitoring unit and the prescription monitoring unit, the controller configured to receive and compare the information recorded by the automated prescription monitoring unit and the prescription monitoring unit;
   wherein the controller is configured to produce a report with information regarding prescriptions recorded by the automated prescription monitoring unit and the prescription monitoring unit, and
   wherein the controller is configured to transmit a recommendation to replace a pharmaceutical dispensed by the automated pharmacy machine with an identified replacement, wherein the recommendation comprises either a recommended adjustment to a bin of the automated pharmacy machine from which the identified replacement is to be dispensed or a recommended replacement of a bin of the automated pharmacy machine from which the pharmaceutical dispensed by the automated pharmacy machine is dispensed.

9. The system defined in claim 8, wherein the automated prescription monitoring unit and the prescription monitoring unit are combined in an overall pharmacy prescription monitoring unit that is configured to record both (i) information regarding prescriptions dispensed by the automated pharmacy machine and (ii) information regarding manually dispensed prescriptions.

10. The system defined in claim 8, wherein the automated prescription monitoring unit is located within the automated pharmacy machine.

11. The system defined in claim 8, wherein at least one of the automated prescription monitoring unit and the prescription monitoring unit is comprises a bar code scanner.

12. The system defined in claim 8, wherein the automated prescription monitoring unit and the prescription monitoring unit are configured to record at least one of: NDC number; DIN number; number of prescriptions filled; and number of tablets dispensed.

13. The system defined in claim 8, further comprising an access device operatively connected with the controller.

14. The system defined in claim 8, wherein at least one of the automated prescription monitoring unit and the prescription monitoring unit is integrated with a pharmacy information system.

15. The system defined in claim 8, wherein one of the automated prescription monitoring unit, the prescription monitoring unit, and the controller is configured to record a time stamp when a prescription is dispensed.

16. The system defined in claim 8, further comprising a second automated prescription monitoring unit associated with a second automated pharmacy machine and a second prescription monitoring unit, the second automated prescription monitoring unit and the second prescription monitoring unit being located at a second remote pharmacy.

17. The system defined in claim 8, wherein the report comprises the recommendation to replace the pharmaceutical dispensed by the automated pharmacy machine with the identified replacement, wherein the report comprises the recommended adjustment to the bin of the automated pharmacy machine from which the identified replacement is to be dispensed, and wherein the controller is configured to transmit the report.

* * * * *

UNITED STATES PATENT AND TRADEMARK OFFICE
CERTIFICATE OF CORRECTION

PATENT NO. : 9,633,172 B2
APPLICATION NO. : 13/682949
DATED : April 25, 2017
INVENTOR(S) : Overfield et al.

Page 1 of 1

It is certified that error appears in the above-identified patent and that said Letters Patent is hereby corrected as shown below:

In the Claims

Column 10, Claim 11, Line 6: Please correct "monitoring unit is comprisies" to read -- monitoring unit comprises --

Signed and Sealed this
Sixth Day of March, 2018

Andrei Iancu
*Director of the United States Patent and Trademark Office*